(12) United States Patent
Duweltz et al.

(10) Patent No.: US 11,613,096 B2
(45) Date of Patent: Mar. 28, 2023

(54) STERILIZABLE MULTILAYER MATERIAL

(71) Applicant: STERIMED SAS, Amelie-les-Bains-Palalda (FR)

(72) Inventors: David Duweltz, Montpellier (FR); Laurent Lebrette, Tressere (FR); Christophe Simon, Maureillas las Illas (FR)

(73) Assignee: STERIMED SAS, Amelie-les-Bains-Palalda (FR)

( * ) Notice: Subject to any disclaimer, the term of this patent is extended or adjusted under 35 U.S.C. 154(b) by 141 days.

(21) Appl. No.: 15/524,436

(22) PCT Filed: Nov. 6, 2015

(86) PCT No.: PCT/EP2015/075983
§ 371 (c)(1),
(2) Date: May 4, 2017

(87) PCT Pub. No.: WO2016/071514
PCT Pub. Date: May 12, 2016

(65) Prior Publication Data
US 2018/0281344 A1 Oct. 4, 2018

(30) Foreign Application Priority Data

Nov. 7, 2014 (FR) ....................................... 1460825

(51) Int. Cl.
*B32B 5/26* (2006.01)
*B32B 3/04* (2006.01)
(Continued)

(52) U.S. Cl.
CPC ................ *B32B 5/26* (2013.01); *A61B 50/30* (2016.02); *B32B 3/04* (2013.01); *B32B 3/266* (2013.01);
(Continued)

(58) Field of Classification Search
CPC .... B32B 3/04; B32B 5/26; B32B 7/05; B32B 7/04; B32B 3/266; B32B 5/022;
(Continued)

(56) References Cited

U.S. PATENT DOCUMENTS 2,649,859 A * 8/1953 Hermanson ........... A61F 13/513
604/366
4,603,069 A * 7/1986 Haq ....................... A45D 37/00
428/76
(Continued)

FOREIGN PATENT DOCUMENTS

GB      1 340 318 A    12/1973
WO     95/01135 A1    1/1995
(Continued)

OTHER PUBLICATIONS

International Search Report and Written Opinion from Corresponding Application No. PCT/EP2015/075983; dated Dec. 4, 2015.
(Continued)

*Primary Examiner* — Catherine A. Simone
(74) *Attorney, Agent, or Firm* — Pearne & Gordon LLP

(57) ABSTRACT

Sterilizable multilayer material (1), in particular for packaging at least one device for medical use, comprising a non-thermofusible sheet (2) sandwiched between two lower and upper thicknesses (3, 4) of thermofusible material of at least one thermofusible sheet (F), these thicknesses of thermofusible material being welded together across the non-thermofusible sheet.

21 Claims, 2 Drawing Sheets

(51) Int. Cl.
  *B32B 3/26* (2006.01)
  *B32B 5/02* (2006.01)
  *A61B 50/30* (2016.01)
  *B32B 7/04* (2019.01)
  *B32B 5/06* (2006.01)
  *B32B 7/14* (2006.01)
  *B32B 29/02* (2006.01)
  *B32B 5/22* (2006.01)
  *B32B 5/08* (2006.01)
  *B32B 29/00* (2006.01)
  *B32B 7/05* (2019.01)
  *B32B 7/027* (2019.01)
  *B32B 37/06* (2006.01)
  *B32B 38/04* (2006.01)
  *A61B 17/00* (2006.01)

(52) U.S. Cl.
  CPC ............... *B32B 5/022* (2013.01); *B32B 5/06* (2013.01); *B32B 5/08* (2013.01); *B32B 5/22* (2013.01); *B32B 7/027* (2019.01); *B32B 7/04* (2013.01); *B32B 7/05* (2019.01); *B32B 7/14* (2013.01); *B32B 29/005* (2013.01); *B32B 29/02* (2013.01); *B32B 37/06* (2013.01); *B32B 38/04* (2013.01); *A61B 2017/00526* (2013.01); *A61B 2050/314* (2016.02); *A61B 2050/316* (2016.02); *B32B 2038/047* (2013.01); *B32B 2262/0253* (2013.01); *B32B 2262/0261* (2013.01); *B32B 2262/0276* (2013.01); *B32B 2262/06* (2013.01); *B32B 2262/062* (2013.01); *B32B 2262/065* (2013.01); *B32B 2262/12* (2013.01); *B32B 2307/31* (2013.01); *B32B 2307/50* (2013.01); *B32B 2307/724* (2013.01); *B32B 2439/80* (2013.01); *B32B 2535/00* (2013.01)

(58) Field of Classification Search
  CPC .... B32B 5/06; B32B 5/08; B32B 5/22; B32B 7/02; B32B 7/14; B32B 29/005; B32B 29/02; B32B 37/06; B32B 38/04; B32B 2038/047; B32B 2262/0253; B32B 2262/0261; B32B 2262/0276; B32B 2262/06; B32B 2262/062; B32B 2262/065; B32B 2262/12; B32B 2307/71; B32B 2307/50; B32B 2307/724; B32B 2439/80; B32B 2535/00; A61B 50/30; A61B 2050/314; A61B 2050/316; A61B 2017/00526; Y10T 428/2419; Y10T 428/24198; Y10T 428/24215; Y10T 428/24231; Y10T 428/2481; Y10T 428/24826; Y10T 428/19; Y10T 428/24777; Y10T 428/183; Y10T 428/163; Y10T 156/1015; Y10T 156/1011; A61L 2/26; A41D 27/24
  USPC ..... 53/425, 461; 422/28; 428/198, 121, 122, 428/192
  See application file for complete search history.

(56) References Cited

U.S. PATENT DOCUMENTS

| | | | |
|---|---|---|---|
| 4,670,073 A | * | 6/1987 | Langley .............. B29C 66/7292 156/73.1 |
| 6,520,184 B2 | * | 2/2003 | Bonnassieux ..... A61F 13/15804 128/849 |
| 2002/0022427 A1 | | 2/2002 | Curro et al. |
| 2006/0052269 A1 | * | 3/2006 | Panandiker ............. A47L 13/17 510/438 |
| 2009/0053103 A1 | | 2/2009 | Mortimer et al. |
| 2011/0192115 A1 | * | 8/2011 | Gammons .............. A61B 50/30 53/167 |
| 2013/0012902 A1 | | 1/2013 | Rovaniemi |

FOREIGN PATENT DOCUMENTS

| | | |
|---|---|---|
| WO | 2007/058822 A1 | 5/2007 |
| WO | 2008/083426 A1 | 7/2008 |
| WO | 2013/068907 A1 | 5/2013 |

OTHER PUBLICATIONS

"Standard Test Method for Seal Strength of Flexible Barrier Materials", F88/F88M, ASTM International West Conshohocken, PA, pp. 897-907, Date: 2009.

\* cited by examiner

STERILIZABLE MULTILAYER MATERIAL

FIELD OF THE INVENTION

The present invention concerns sterilization sheets and the multilayer materials made from such sheets.

BACKGROUND OF THE INVENTION

Sterilization sheets are primarily used at the sterilization centers of hospitals and healthcare facilities to wrap medical devices, especially reusable ones, freshly washed and disinfected, such as scalpels, forceps, scissors, endoscopes, basins, trays, or tongue depressors.

One commonly uses two sterilization sheets one placed on top of the other in order to wrap a medical device so as to guarantee its sterility up to the time of use.

Sterilization sheets are generally made of special papers or thermoplastic materials. Patent application WO 2007/058822 for example describes papers having improved microbial barrier properties for use in a sterile packaging.

A sterilization sheet should meet the general requirements as described in the international standard ISO 11607-1:06: "Packagings for medical devices sterilized in the terminal stage—Part 1: Requirements on the materials, the sterile barrier systems, and the packaging systems", defining in particular the microbial barrier properties and the compatibility with the sterilization process.

The performance of sterilization sheets is also described in the European standard EN 868-2:09: "Packaging materials and systems for medical devices sterilized in the terminal stage—Part 2: sterilization envelope—requirements and test methods".

The known sterilization sheets may be made of nonwoven material and of crepe paper, for example standard crepe paper or microcrepe paper composed primarily of wood pulp and additives; reinforced crepe paper composed primarily of wood pulp, additives, and synthetic binders; "nonwoven wet-laid materials" composed of a mixture of wood pulp, binders, additives and hydrophobic synthetic fibers; or "nonwoven melt-blown materials" composed of 100% synthetic fibers, especially polypropylene, known by the generic name of "SMS" (Spunbond-Meltblown-Spunbond or also Spun-Melt-Spun).

In order to save time for the user, it is proposed in the patent applications WO95/01135 and WO2013/068907, which disclose sterilization sheets each comprising a thermoplastic compound of SMS type, to weld the two sheets together.

The combining of a non-thermofusible cellulose sheet and a thermofusible synthetic sheet based on thermoplastic compounds, especially of SMS type, would make it possible to reconcile the properties of a bacterial barrier, essentially provided by the cellulose sheet, and mechanical protection, essentially provided by the sheet based on thermoplastic compounds.

Now, it is at present impossible to directly weld a cellulose sheet to a thermofusible sheet of SMS type in permanent fashion, a welding by heat or ultrasound not allowing the production of sufficient bonding forces between these two types of sheets, with different thermal fusion properties.

One solution involves the use of an adhesive. However, the introduction of an adhesive causes an additional cost, a decrease in sterilization stability, a risk of contamination of the medical devices as well as an additional packaging stage.

The invention intends to remedy this drawback.

BRIEF SUMMARY OF THE INVENTION

Thus, the purpose of the invention, according to a first aspect, is a sterilizable multilayer material, in particular for packaging at least one device for medical use, comprising a non-thermofusible sheet sandwiched between two thicknesses of thermofusible material of at least one thermofusible sheet, these thicknesses of thermofusible material being welded together across the non-thermofusible sheet.

The multilayer material so obtained meets the aforementioned standards ISO 11607-1:06 and EN 868-2:09.

Thus, it is sufficiently porous to allow the passage of a sterilization gas while offering the required bacterial barrier.

Surprisingly, it is possible to attach the non-thermofusible sheet to one or more thermofusible sheets by welding the two thicknesses of thermofusible material together across the non-thermofusible sheet.

The notion of overlapping between two sheets or the face of one sheet by another sheet in the present invention may or may not involve a contact between the two sheets.

The non-thermofusible sheet or sheets, especially when made of cellulosic webs, may be degraded by the energy of the welding, in clean manner without generating residues, which may allow the thermofusible material of the superimposed thicknesses to diffuse across the non-thermofusible sheet, and obtain a mechanically strong weld after cooldown.

By "thermofusible sheet" is meant a sheet composed for the most part, or better exclusively, of thermofusible compounds, preferably those fluidifiable at a temperature less than or equal to 300° C., or better 250° C.

By "non-thermofusible sheet" is meant a sheet without a thermofusible compound, or one whose total content of thermofusible compounds is insufficient to produce a strong weld if one tries to weld the sheet to itself, especially in order to obtain a weld whose sealing strength is greater than or equal to 100 cN/15 mm, according to the standard ASTM F88.

The non-thermofusible sheet is preferably composed of a cellulosic web, as detailed below.

Multilayer Material

By "thickness of thermofusible material" of a thermofusible sheet is meant a region of that sheet.

The thicknesses of thermofusible material which are placed one on top of the other and welded across the non-thermofusible sheet may belong to the same thermofusible sheet or not. When they belong to the same thermofusible sheet, one of the thicknesses is formed by a flap of this sheet, which is then folded onto itself and onto the non-thermofusible sheet.

In the following, in order to distinguish the two thicknesses of thermofusible material between which the non-thermofusible sheet is sandwiched, these thicknesses shall be qualified as "upper" and "lower" in order to designate respectively the one covering the upper face and the one covering the lower face of the non-thermofusible sheet.

The upper face of the non-thermofusible sheet of the multilayer material may be only partly covered by the upper thickness of thermofusible material.

The lower face of the non-thermofusible sheet of the multilayer material may be totally covered by the lower thickness of thermofusible material.

As mentioned above, the upper thickness of thermofusible material and the lower thickness of thermofusible material of the multilayer material may belong to the same thermofusible sheet. This sheet is thus welded to itself across the non-thermofusible sheet.

The non-thermofusible sheet may have two opposite edges, in particular parallel edges, and the thermofusible sheet may be folded on either side of the non-thermofusible sheet along said edges.

The non-thermofusible sheet may have four edges, in particular, edges parallel in pairs, and the thermofusible sheet may be folded onto itself along one, two, three or four of said edges.

The thermofusible sheet preferably has a width greater than that of the non-thermofusible sheet, so as to be folded onto the edges of the latter and contain the non-thermofusible sheet in sandwich fashion.

The thermofusible sheet may totally cover the lower face of the non-thermofusible sheet and be folded over onto the upper face of the latter, especially onto its opposite edges.

The multilayer material may have a sealing strength, according to the aforesaid standard ASTM F88 "Standard Test Method for Seal Strength of Flexible Barrier Materials", greater than or equal to 100 cN/15 mm, or better 300 cN/15 mm, or even better greater than or equal to 500 cN/15 mm.

Such a sealing strength makes it possible to hold together the different sheets making up the product during the phases of packaging, sterilization and storage.

The multilayer material is advantageously devoid of an adhesive used to assemble the sheets together and applied to them. The absence of an adhesive reduces the risk of cytotoxicity of the multilayer material.

The multilayer material is preferably compatible with a process of sterilization by EtO gas and/or by steam and/or by dry heat and/or by low-temperature formaldehyde steam (LTFS) and/or any other nonoxidative sterilization process.

The multilayer material is preferably intended to package at least one medical device, especially a reusable one. The medical device to be packaged may be arranged on the upper face of the non-thermofusible sheet, and then the multilayer material can be folded around the medical device to envelop it.

The multilayer material according to the invention also allows the producing of a sterile operative field, according to the standards EN 13795 and/or AAMI BP 70.

Non-Thermofusible Sheet

In the following, the basis weights are defined in accordance with the standard ISO 536.

The non-thermofusible sheet is preferably a sheet based on cellulose fibers.

It may be a nonwoven material or a paper, preferably one made from cellulosic wood fibers, or other plant materials such as cotton, hemp, linen, bamboo, among other plants.

In the case of a nonwoven material, the sheet may be a web obtained by a dry process, so-called "airlaid", comprising for example 100% of chemically consolidated cellulose fibers.

It may also be a nonwoven material obtained by a wet process, comprising for example cellulose fibers and synthetic fibers, especially fibers of PET, PP or PA, and one or more synthetic binders, such as acrylic, vinylic or styrenic binders, especially those based on styrene butadiene.

It may further be a nonwoven material consolidated mechanically by so-called "spunlace", comprising cellulose fibers and synthetic fibers.

In the case of a paper, it can be a 100% cellulosic paper, or a so-called "latexed" paper, reinforced with the aid of one or more synthetic binders such as acrylic, vinylic or styrenic binders, especially those based on styrene butadiene.

In all cases, the total content of thermofusible compounds of the non-thermofusible sheet is insufficient to render it capable of a sealing on itself with the desired sealing strength, especially greater than or equal to 100 cN/15 mm.

In particular, the total content of thermofusible compounds, especially thermoplastic ones, may be less than 50% of the total weight of the non-thermofusible sheet, or preferably 30%.

The preferred weight of the non-thermofusible sheet depends on its nature.

Preferably, for a non-thermofusible sheet of nonwoven material of airlaid type, the weight is between 15 and 100 g/m$^2$, preferably ranging from 30 to 50 g/m$^2$.

For a nonwoven material of spunlace type, the weight is preferably less than 100 g/m$^2$, preferably 50 g/m$^2$.

For a paper, especially a 100% cellulosic, or latexed paper, or for a nonwoven material obtained by the wet process, the weight is preferably less than or equal to 100 g/m$^2$, preferably 80 g/m$^2$, more preferably 60 g/m$^2$.

The non-thermofusible sheet may be a crepe paper.

The non-thermofusible sheet has a fibrous structure presenting a sufficiently dense tangle of fibers to ensure a barrier action with respect to bacteria, while being sufficiently porous and breathable to let through gases, especially those used for the sterilization. It should not re-release a substance.

The non-thermofusible sheet may be of different color from that of the thermofusible sheet.

Thermofusible Sheet

The thermofusible sheet has a total content of thermofusible compounds sufficient to obtain the desired combination. This content is preferably greater than or equal to 50% by weight, preferably 90%.

The thermofusible compound or compounds of the thermofusible sheet are preferably thermoplastic compounds.

The thermofusible sheet or sheets of the multilayer material may thus be constituted by one or more thermoplastic compounds.

The thermofusible sheet or sheets may be defined by a nonwoven material comprising only thermofusible fibers, especially thermoplastic ones.

It may be a nonwoven material consolidated by a dry process, by a wet process, or by a melt process.

In the case of the melt process, it may be a "spun bond" or a "melt blown" material, these nonwoven materials being obtained by extrusion of fibers and then thermal consolidation by hot rolling or ultrasound, or any combination of these nonwoven materials.

The thermofusible sheet may thus comprise one or more layers of type "Spun" or "Melt", in particular, it may be a sheet of type "Spun" or "Spun-Spun" (SS) or "Spun-Spun-Spun" (SSS) or "Spun-Melt-Spun" (SMS) or "Spun-Spun-Melt-Spun" (SSMS) or "Spun-Melt-Melt-Spun" (SMMS), or "Melt-Melt" (MM) or "Melt-Melt-Melt" (MMM) or "Spun-Spun-Melt-Melt-Melt-Spun" (SSMMMS) and other combinations of the "Spun" and "Melt" technologies.

The thermofusible sheet or sheets may comprise, or in particular be constituted of, a polypropylene PP, a PET, a PA, a PE, a PP-PE, and/or a PLA, preferably a PP, or any other biodegradable thermofusible polymer.

The thermofusible sheet may also comprise binary fibers of core/shell type, especially made from PET/PE or PP/PE.

The thermofusible sheet or sheets may have a weight between 10 and 100 g/m$^2$, preferably between 30 and 60 g/m$^2$.

Welding

The non-thermofusible sheet may have two edges, in particular parallel edges, and the welding may be done at least along at least part of at least one of the edges of the sheet, preferably along at least part of each of the two edges.

When the upper thickness of thermofusible material and the lower thickness of thermofusible material are formed by the same thermofusible sheet and the non-thermofusible sheet comprises two opposite and parallel edges, the thermofusible sheet may be folded on either side of the non-thermofusible sheet along said edges and welded.

The welding may be done along one or more welding lines, being continuous or discontinuous along each welding line.

The width of a welding line may be between 1 and 100 mm, preferably between 2 and 10 mm.

The welding is preferably an ultrasound welding.

The footprint of the weld may comprise, in particular be composed of one or more continuous and/or discontinuous lines, and/or patterns, etc.

The welding may also be a welding by conduction, by laser, or by hot gas heating.

Prior to the welding step, perforations may be made in the non-thermofusible sheet, with the aid of a laser for example. Such perforations may facilitate the passage of the thermofusible material through the non-thermofusible sheet.

The welding may be done without prior perforations.

Supplemental Sheets

The multilayer material may comprise one or more supplemental non-thermofusible sheets and/or one or more additional thermofusible sheets.

The supplemental non-thermofusible sheets may be arranged between said lower thickness of thermofusible material and said upper thickness of thermofusible material, which are then welded to each other across the supplemental non-thermofusible sheet or sheets. The lower thickness and the upper thickness of thermofusible material are advantageously formed by the same thermofusible sheet.

The multilayer material may comprise one or more supplemental thermofusible sheets.

The multilayer material may comprise a first thermofusible sheet, holding in sandwich fashion a first non-thermofusible sheet and optionally one or more supplemental non-thermofusible sheets, especially along a first edge of the first non-thermofusible sheet.

A second thermofusible sheet may hold in sandwich fashion the first non-thermofusible sheet and optionally one or more supplemental non-thermofusible sheets, thanks to a welding across these sheets, along a second edge of the first non-thermofusible sheet, this second edge being in particular parallel to the first edge.

One may thus secure the first non-thermofusible sheet to the supplemental non-thermofusible sheet or sheets by holding them all in sandwich fashion on at least one, especially two of their edges, by the thermofusible sheet or sheets.

Such a multilayer material makes it possible to immobilize two non-thermofusible sheets between them without the need for adding an adhesive.

The outermost sheet or sheets of the multilayer material may be defined by one or more thermofusible sheets. The non-thermofusible sheet or sheets may thus be held in sandwich fashion between one or more outer thermofusible sheets covering all or part of the non-thermofusible sheet or sheets.

The multilayer material may comprise a supplemental non-thermofusible sheet, known as the upper non-thermofusible sheet, having an upper face and a lower face, the aforesaid upper thickness of thermofusible material being partly or totally covered by the lower face of the upper non-thermofusible sheet, the upper face of the upper non-thermofusible sheet being partly or totally covered by a thickness of thermofusible material known as the upper thickness of thermofusible material of second rank, the upper thickness of thermofusible material and the upper thickness of thermofusible material of second rank being both welded together across the upper non-thermofusible sheet.

The multilayer material may comprise a supplemental non-thermofusible sheet, known as the lower non-thermofusible sheet, having an upper face and a lower face, the aforesaid lower thickness of thermofusible material being partly or totally covered by the upper face of the lower non-thermofusible sheet, the lower face of the lower non-thermofusible sheet being partly or totally covered by a thickness of thermofusible material known as the lower thickness of thermofusible material of second rank, the lower thickness of thermofusible material and the lower thickness of thermofusible material of second rank being both welded together across the lower non-thermofusible sheet.

The upper non-thermofusible sheet and/or the lower non-thermofusible sheet and/or more generally each supplemental non-thermofusible sheet may each have one or more of the characteristics described above regarding the non-thermofusible sheet.

The upper thermofusible sheet of second rank and/or the lower thermofusible sheet of second rank and/or more generally each supplemental thermofusible sheet may each have one or more of the characteristics described above regarding the thermofusible sheet or sheets defining the aforesaid upper and lower thicknesses of thermofusible material.

The welding of the upper thickness of thermofusible material to the upper thickness of thermofusible material of second rank may be overlapping that of the upper thickness of thermofusible material on the lower thickness of thermofusible material. As a variant, the welding of the upper thickness of thermofusible material to the upper thickness of thermofusible material of second rank may not be overlapping that of the upper thickness of thermofusible material on the lower thickness of thermofusible material.

The welding of the lower thickness of thermofusible material to the lower thickness of thermofusible material of second rank may be overlapping that of the upper thickness of thermofusible material on the lower thickness of thermofusible material. As a variant, the welding of the lower thickness of thermofusible material to the lower thickness of thermofusible material of second rank may not be overlapping that of the upper thickness of thermofusible material on the lower thickness of thermofusible material.

Packaging

The invention also in another of its aspects relates to a combination comprising a multilayer material according to the invention and at least one device for medical use, especially one in a sterile condition.

The multilayer material may be folded around the medical device by a folding of the envelope or square type for example.

Fabrication Method

The invention also in another of its aspects relates to a method of fabrication of a multilayer material according to the invention, comprising a step in which one welds, preferably by ultrasound, the upper thickness of thermofusible material to the lower thickness of thermofusible material across the non-thermofusible sheet. The latter might not be microperforated in advance in the assembly zone. As a variant, a first step of perforation of the non-thermofusible sheet is provided.

The welding step can be done advantageously in a line.

The method of fabrication may involve a step, prior to the welding step, in which a welding station, especially an ultrasound welding station, is placed on a winding machine.

When the lower thickness of thermofusible material and the upper thickness of thermofusible material are formed by the same thermofusible sheet, the method of fabrication may involve a step, especially one in a line, prior to the welding step, in which at least one side, especially two sides of the thermofusible sheet, is folded over onto itself, especially by a rail system, so as to grasp the non-thermofusible sheet in sandwich fashion.

The ultrasound frequency may be between 10 kHz and 100 kHz, preferably between 20 and 40 kHz.

The ultrasound may allow a degrading of the non-thermofusible sheet, in particular, the creating of passages for the thermofusible material, and produce a heating which enables a welding of the upper thickness of thermofusible material to the lower thickness of thermofusible material across the non-thermofusible sheet so immobilized.

The ultrasound may be generated by a generator connected to an acoustical unit comprising a converter designed to transform the electrical energy furnished by the generator into mechanical vibration, an amplifier designed to amplify the mechanical vibration, and a sonotrode designed to transfer the mechanical vibration to the multilayer material.

The method may involve a static or rotary welding system. The choice of the system may depend on the mode of production adopted, in particular single unit or continuous, the desired speed of production, and the intended quality of the welding.

The ultrasound welding enables an economical work process, continuous and at very high speed, with precision. It is likewise possible to use thermal welding machines or a laser.

In one sample embodiment of the method:
a. the non-thermofusible sheet is perforated, especially by microperforation, then
b. the upper thickness of thermofusible material and the lower thickness of thermofusible material are heat bonded, especially through the perforations of the non-thermofusible sheet.

BRIEF DESCRIPTION OF THE DRAWINGS

The invention may be better understood upon perusal of the following detailed description of nonlimiting sample embodiments and an examination of the appended drawing, in which.

DESCRIPTION OF EXAMPLE EMBODIMENTS

In FIGS. 1 to 10, the different component parts have been shown schematically before assembly. The real proportions are not always obeyed, for reasons of clarity.

Figure 1:
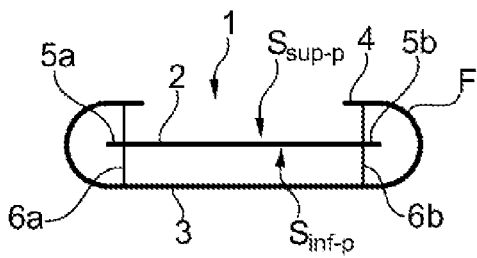
FIG. 1 shows, in cross section and schematically, an example of multilayer material according to the invention.

FIG. 1 shows a multilayer material 1 for the packaging of at least one device for medical use according to the invention.

The material comprises a non-thermofusible sheet 2 having a lower face $S_{inf\text{-}p}$ and an upper face $S_{sup\text{-}p}$. This non-thermofusible sheet is preferably a nonwoven material or a cellulosic paper, as detailed above.

The lower face $S_{inf\text{-}p}$ is covered by a lower thickness of thermofusible material 3, and the upper face $S_{sup\text{-}p}$ is covered by an upper thickness of thermofusible material 4.

The lower thickness of thermofusible material and the upper thickness of thermofusible material are formed here by the same thermofusible sheet F, in contact with the non-thermofusible sheet 2.

The thermofusible sheet F thus covers entirely the lower face $S_{inf\text{-}p}$ of the non-thermofusible sheet 2 and partly its upper face $S_{sup\text{-}p}$.

The thermofusible sheet F is folded over on either side of the non-thermofusible sheet 2, and holds it in sandwich fashion.

The non-thermofusible sheet 2 has two parallel edges 5a and 5b, along which the sheet F is folded.

The sheet F is welded to itself along the two edges 5a and 5b of the sheet 2, along two welding lines 6a and 6b, across the sheet 2. In the area of the welding, the multilayer material thus contains three thicknesses one on top of the other.

One may thus seal a thermofusible sheet F comprising a thermoplastic compound, especially one of type SMS, to a non-thermofusible cellulosic sheet 2, despite their incompatibility for direct welding. This is made possible thanks to the sandwiching of the non-thermofusible sheet by the sheet F, the latter being folded over in the manner of a hem.

In order to weld the sheet F to itself across the sheet 2, one positions the sheet 2 on the sheet F. This latter has a width greater than that of the sheet 2, so that it can be folded over along the edges of the latter and grasp it in sandwich fashion.

The upper and lower portions of the sheet F can thus be welded together at an ultrasound welding station.

Figure 7:
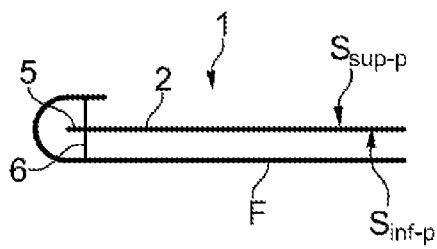

FIG. 7 illustrates a variant of the material according to the invention, wherein the sheet F is folded over and welded solely along one edge of the sheet 2.

Figure 8:
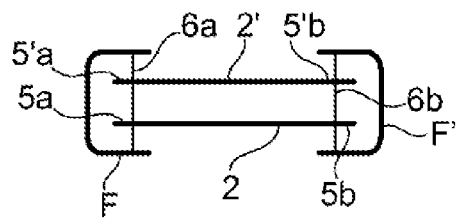

In the example of FIG. 8, the multilayer material 1 comprises a supplemental non-thermofusible sheet 2' covering the sheet 2 and being grasped in sandwich fashion with it, along its edge 5'a, by the sheet F welded to itself along a welding line 6a.

The multilayer material 1 likewise comprises a second thermofusible sheet F', which grasps in sandwich fashion the sheet 2 and the supplemental sheet 2', along their respective edges 5b and 5'b, the portions placed one on top of the other being welded along a welding line 6b.

Thus, the sheet 2 and the supplemental sheet 2' are secured at their edges by the sheets F and F'. This makes it possible to assemble two non-thermofusible sheets 2 and 2' without adding adhesive.

The multilayer material of FIG. 8 is lacking in the second sheet F' in one embodiment not shown.

Figure 6:
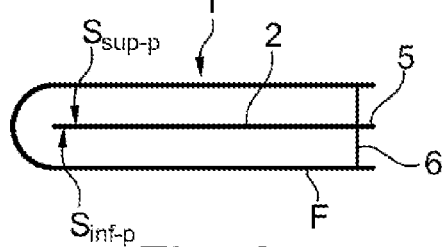

FIG. 6 illustrates an example of multilayer material 1 according to the invention in which the lower thickness of thermofusible material 3 and the upper thickness of thermofusible material 4 come from the same sheet F folded on either side of the sheet 2, covering entirely the upper face $S_{sup\text{-}p}$ and lower face $S_{inf\text{-}p}$ of the sheet 2. The welding 6 is done along one edge 5 of the sheet 2, on the side opposite the folding of the sheet F.

FIGS. 2 to 5 illustrate variants of the multilayer material 1 according to the invention, in which the lower thickness of thermofusible material 3 and the upper thickness of thermofusible material 4 are formed from distinct thermofusible sheets.

Figure 2:
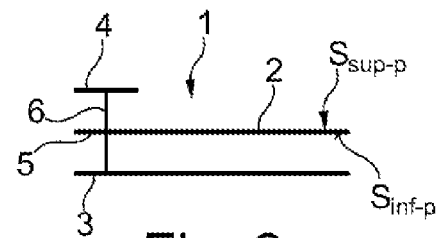
FIGS. 2 to 10 show, in cross section and schematically, variant examples of multilayer material according to the invention.
Figure 3:
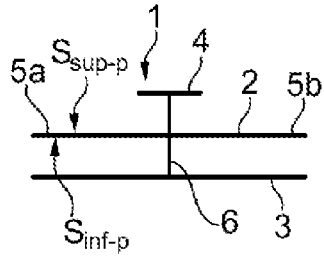
Figure 4:
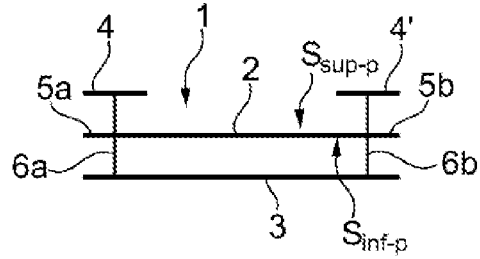

FIGS. 2 to 4 illustrate a multilayer material 1 in which the upper thickness of thermofusible material 4 partly covers the sheet 2.

In the example of FIG. 2, the welding 6 is done along an edge 5 of the sheet 2. In the example of FIG. 3, it is done substantially in the center of the sheet 2.

In the example of FIG. 4, the multilayer material comprises a second upper thermofusible sheet 4'. The welding 6 is done along the two edges 5a and 5b of the sheet 2, between the upper thickness of thermofusible material 4 and the lower thickness of thermofusible material 3 on the one hand, and between the second upper sheet 4' and the lower thickness of thermofusible material 3 on the other hand.

Figure 5:
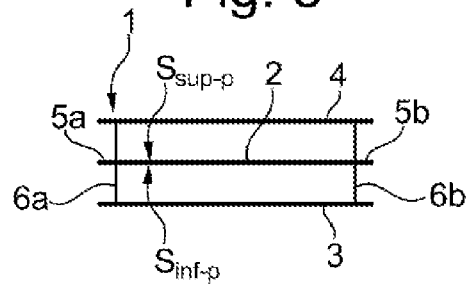

In the example of FIG. 5, the upper thickness of thermofusible material 4 entirely covers the sheet 2 and the welding is done along opposite edges 5a and 5b of the sheet 2.

Figure 9:
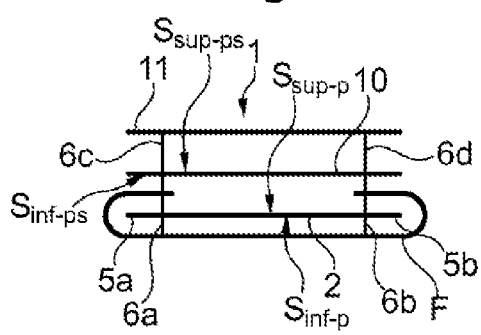

FIG. 9 shows an example of multilayer material 1 comprising a sheet 2 and a sheet F as previously described in reference to FIG. 1.

The multilayer material 1 furthermore comprises a supplemental upper non-thermofusible sheet 10, and a supplemental upper thermofusible sheet of second rank 11.

The multilayer material 1 has welds 6c, 6d of the sheet F to the upper sheet of second rank 11 across the upper non-thermofusible sheet 10, situated on top of the welds 6a, 6b of the sheet F to itself across the sheet 2.

Figure 10:
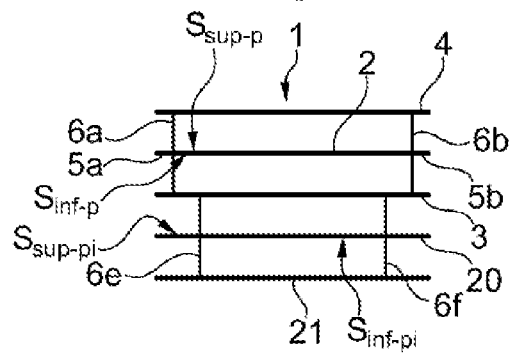

FIG. 10 illustrates an example of multilayer material 1 comprising a non-thermofusible sheet 2, an upper thermofusible sheet 4 and a lower thermofusible sheet 3 as described previously in reference to FIG. 5.

The multilayer material 1 furthermore comprises a supplemental lower non-thermofusible sheet 20, and a supplemental lower thermofusible sheet of second rank 21.

The multilayer material 1 has welds 6e, 6f of the lower sheet 3 to the lower sheet of second rank 21 across the lower sheet 20. These welds 6e, 6f are not situated on top of the welds 6a, 6b of the upper sheet 4 to the lower sheet 3 across the sheet 2.

The outermost sheets 4 and 21 of the multilayer material 1 are thermofusible.

Figure 11:
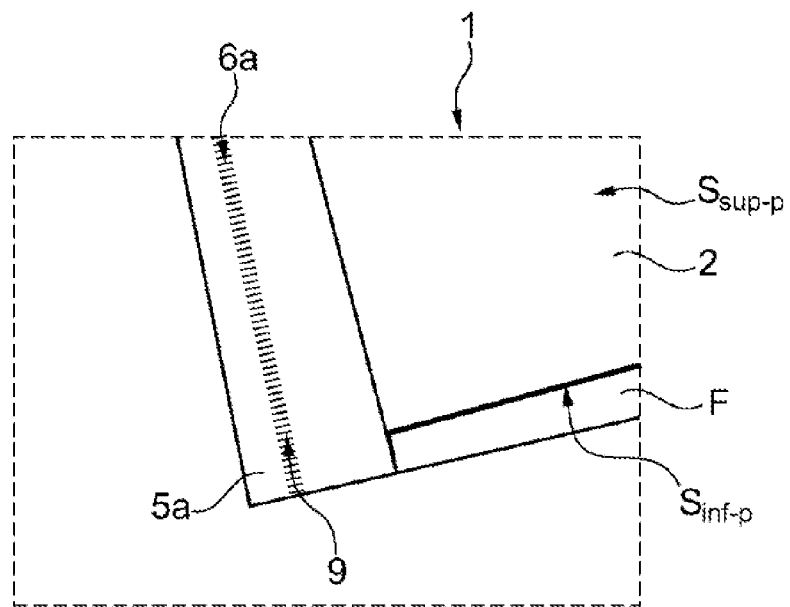
FIG. 11 illustrates, in top view, part of the multilayer material of FIG. 1.
Figure 12:
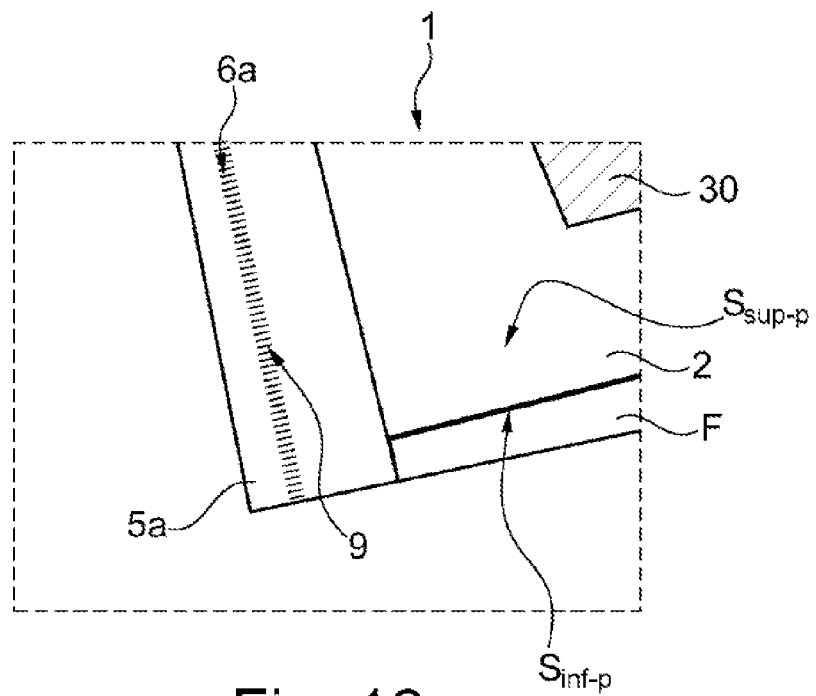
FIG. 12 represents the part of the multilayer material of the preceding figure on which is arranged, in schematic manner, part of a medical device ready to be packaged.

FIGS. 11 and 12 show in top view a portion of the multilayer material 1 of FIG. 1. FIG. 12 also shows a medical device 30 to be packaged, placed on the upper face $S_{sup-p}$ of the non-thermofusible sheet 2. The welding 6a along the edge 5a of the sheet 2 is in the form of a discontinuous welding line.

Of course, the invention is not limited to the examples illustrated and in particular one can combine the characteristics of the examples illustrated within variants which have not been illustrated.

The term "comprising a" should be understood as being synonymous with "comprising at least one", unless otherwise stipulated.

The invention claimed is:

1. A sterilizable multilayer material, comprising a non-thermofusible sheet sandwiched between two lower and upper thicknesses of thermofusible material of at least one thermofusible sheet, these thicknesses of thermofusible material being welded together through the non-thermofusible sheet, an upper face of the non-thermofusible sheet being only partly covered by the upper thickness of thermofusible material, a lower face of the non-thermofusible sheet being totally covered by the lower thickness of thermofusible material, the thicknesses of thermofusible material together being defined by a single thermofusible sheet, the thermofusible sheet being chosen from among nonwoven materials consolidated by a wet process, by a dry process, or by a melt process.

2. The material as claimed in claim 1, the thermofusible sheet being defined by a sheet of nonwoven material consolidated by a melt process.

3. The multilayer material as claimed in claim 1, the non-thermofusible sheet being chosen from among nonwoven materials and papers.

4. The multilayer material as claimed in claim 1, the non-thermofusible sheet having two edges, the welding being done at least along at least part of at least one of said edges of the non-thermofusible sheet.

5. The multilayer material as claimed in claim 1, the non-thermofusible sheet having two edges, the thermofusible sheet being folded over on either side of the non-thermofusible sheet along its said edges and welded along at least part of said edges.

6. The multilayer material as claimed in claim 1, the welding being done along one or more welding lines, the welding being continuous or discontinuous along each welding line.

7. The multilayer material as claimed in claim 1, the multilayer material being devoid of adhesive between the assembled layers.

8. The multilayer material as claimed in claim 1, wherein the thicknesses of the thermofusible material extend along an outer edge of the non-thermofusible sheet and inwardly from said outer edge in order to only partly cover at least one major face of the non-thermofusible sheet with said at least one major face also being at least partly exposed.

9. The multilayer material as claimed in claim 1, the non-thermofusible sheet comprising cellulose fibers.

10. A method of fabrication of a multilayer material as claimed in claim 1, involving a step in which the upper thickness of thermofusible material is welded to the lower thickness of thermofusible material through the non-thermofusible sheet.

11. The method as claimed in claim 10, wherein the welding is done by ultrasound.

12. The method as claimed in claim 10, wherein the welding is done by conduction, laser or hot gas.

13. The method of fabrication as claimed in claim 10, wherein the lower thickness of thermofusible material and the upper thickness of thermofusible material are defined by the same thermofusible sheet, the method involving a step prior to the welding step, in which the thermofusible sheet is folded over onto itself so as to grasp the non-thermofusible sheet in sandwich fashion.

14. The method as claimed in claim 10, the non-thermofusible sheet not undergoing a microperforation prior to the welding in the zone where the lower and upper thicknesses of thermofusible material are overlapping.

15. The method as claimed in claim 10, wherein the non-thermofusible sheet undergoes a microperforation step prior to the welding in the zone where the lower and upper thicknesses of thermofusible material are overlapping.

16. A combination of a multilayer material as claimed in claim 1 and at least one device for medical use, wrapped in said material in a sterile condition.

17. An operative field comprising a multilayer material as claimed in claim 1.

18. A sterilizable multilayer material, comprising a non-thermofusible sheet sandwiched between two lower and upper thicknesses of thermofusible material of at least one thermofusible sheet, these thicknesses of thermofusible material being welded together through the non-thermofusible sheet, an upper face of the non-thermofusible sheet being only partly covered by the upper thickness of thermofusible material, a lower face of the non-thermofusible sheet being totally covered by the lower thickness of thermofusible material, the thicknesses of thermofusible material together being defined by a single thermofusible sheet, the multilayer material having a sealing strength, as claimed in the standard ASTM F88, greater than or equal to 100 cN/15 mm.

19. A sterilizable multilayer material, comprising a non-thermofusible sheet sandwiched between two lower and upper thicknesses of thermofusible material of at least one thermofusible sheet, these thicknesses of thermofusible material being welded together through the non-thermofusible sheet, an upper face of the non-thermofusible sheet being only partly covered by the upper thickness of thermofusible material, a lower face of the non-thermofusible sheet being totally covered by the lower thickness of thermofusible material, the thicknesses of thermofusible material together being defined by a single thermofusible sheet, the multilayer material comprising a supplemental upper non-thermofusible sheet, having an upper face and a lower face, the upper thickness of thermofusible material being partly or totally covered by the lower face of the supplemental upper non-thermofusible sheet, the upper face of the supplemental upper non-thermofusible sheet being partly or totally covered by an upper thickness of thermofusible material of second rank, the upper thickness of thermofusible material and the upper thickness of thermofusible material of second rank being welded together across the supplemental upper non-thermofusible sheet.

20. A sterilizable multilayer material, comprising a non-thermofusible sheet sandwiched between two lower and upper thicknesses of thermofusible material of at least one thermofusible sheet, these thicknesses of thermofusible material being welded together through the non-thermofusible sheet, an upper face of the non-thermofusible sheet being only partly covered by the upper thickness of thermofusible material, a lower face of the non-thermofusible sheet being totally covered by the lower thickness of thermofusible material, the thicknesses of thermofusible material together being defined by a single thermofusible sheet, the multilayer material comprising a supplemental non-thermofusible sheet, having an upper face and a lower face, the lower thickness of thermofusible material being partly or totally covered by the upper face of a supplemental lower non-thermofusible sheet, the lower face of the supplemental lower non-thermofusible sheet being partly or totally covered by a lower thickness of thermofusible material of second rank, the lower thickness of thermofusible material and the lower thickness of thermofusible material of second rank being welded together across the supplemental lower non-thermofusible sheet.

21. A sterilizable multilayer material, comprising a non-thermofusible sheet sandwiched between two lower and upper thicknesses of thermofusible material of at least one thermofusible sheet, these thicknesses of thermofusible material being welded together through the non-thermofusible sheet, an upper face of the non-thermofusible sheet being only partly covered by the upper thickness of thermofusible material, a lower face of the non-thermofusible sheet being totally covered by the lower thickness of thermofusible material, the thicknesses of thermofusible material together being defined by a single thermofusible sheet, wherein the non-thermofusible sheet includes perforations therethrough, allowing the thicknesses of thermofusible material to be welded together through the non-thermofusible sheet.

* * * * *